US007193214B1

(12) United States Patent
Pittman

(10) Patent No.: US 7,193,214 B1
(45) Date of Patent: Mar. 20, 2007

(54) SENSOR HAVING DIFFERENTIAL POLARIZATION AND A NETWORK COMPRISED OF SEVERAL SUCH SENSORS

(75) Inventor: William C. Pittman, Huntsville, AL (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 65 days.

(21) Appl. No.: 11/109,022

(22) Filed: Apr. 8, 2005

(51) Int. Cl.
*H01L 25/00* (2006.01)
*G01J 4/00* (2006.01)
*G02F 1/01* (2006.01)

(52) U.S. Cl. .................. 250/341.3; 250/330; 250/351; 250/332

(58) Field of Classification Search ................ 250/351, 250/330, 341.3
See application file for complete search history.

(56) References Cited

U.S. PATENT DOCUMENTS

| 5,373,320 | A |   | 12/1994 | Johnson et al. ............. 348/217 |
| 5,386,119 | A | * | 1/1995  | Ledger ..................... 250/341.8 |
| 5,416,324 | A | * | 5/1995  | Chun ....................... 250/341.3 |
| 5,483,066 | A | * | 1/1996  | Sadjadi et al. ............ 250/338.1 |
| 5,557,261 | A | * | 9/1996  | Barbour ....................... 340/580 |
| 5,975,702 | A |   | 11/1999 | Pugh, Jr. et al. ............ 351/246 |
| 6,023,061 | A | * | 2/2000  | Bodkin ........................ 250/332 |
| 6,075,235 | A | * | 6/2000  | Chun ....................... 250/208.1 |
| 6,310,345 | B1 | * | 10/2001 | Pittman et al. ............. 250/334 |
| 6,563,582 | B1 | * | 5/2003  | Chun ......................... 356/364 |
| 6,583,415 | B2 | * | 6/2003  | Stevens ...................... 250/330 |
| 6,987,256 | B2 | * | 1/2006  | English et al. ........... 250/203.6 |
| 2002/0180866 | A1 | * | 12/2002 | Monroe ....................... 348/153 |

OTHER PUBLICATIONS

"Time Series Processing of FLIR Imagery for MTI and Change Detection" by Mehrdad Soumekh, S. Susan Young and Nasser M. Nasrabadi, in the IEEE's *Proceedings of the International Conference on Acoustics, Speech and Signal Processing*, Apr. 6-10, 2003, vol. 5, pp. 21-24 (2003).

"Registration of Image Cubes Using Multivariate Mutual Information," by Jeffrey P. Kern et al in IEEE's *Thirty-Seventh ASILOMAR Conference: Signals, Systems and Computers*, Nov. 9-12, 2003, vol. 2, pp. 1645-1649 (2003).

(Continued)

*Primary Examiner*—Albert Gagliardi
(74) *Attorney, Agent, or Firm*—Hay Kyung Chang

(57) ABSTRACT

Parametric processing capability is added to a typical sensor so that a target object can be more clearly distinguished from the background clutter in a given scenery. A polarizer with several segments of different polarization orientations is used to improve the typical sensor. The segments are sequentially advanced to pass therethrough infrared radiation images of pre-selected polarization orientations which are then collected by respective polarized frame grabbers. Image processing circuit processes these images to yield the polarization difference between any given pair of orthogonal polarizations. In a surveillance network, the polarization differences are subsequently used in the control center, to which such sensors are connected, to enhance the distinction of the observed objects against the background clutter suspended in the propagation medium.

5 Claims, 4 Drawing Sheets

OTHER PUBLICATIONS

"Multiple Single Pixel Dim Target Detection in Infrared Image Sequence," by Mukesh A. Zaveri et al in IEEE's *Proceedings of International Conference on Circuits and Systems*, May 25-28, 2003, vol. 2, pp. II-380 to II-383 (2003)

U.S. Appl. No. (as yet unpublished) 10/853,748 filed May 24, 2004, Art Unit 2878. Invention Title: Polarized Semi-Active Laser Last Pulse Logic Seeker Using a Starting Focal Plane Array; Inventors: James E. English and William C. Pittman.

* cited by examiner

US 7,193,214 B1

SENSOR HAVING DIFFERENTIAL POLARIZATION AND A NETWORK COMPRISED OF SEVERAL SUCH SENSORS

DEDICATORY CLAUSE

The invention described herein may be manufactured, used and licensed by or for the Government for governmental purposes without the payment to me of any royalties thereon.

BACKGROUND OF THE INVENTION

In these times of heightened security, there are many instances when particular geographic areas may need to be placed under surveillance to protect potential targets from terrorist attacks or as an adjunct to military operations.

When an object is imbedded in a medium such as rain or fog, the presence of scatterers in the medium causes the image of the object to appear indistinct or blurred, making object detection difficult. One aspect of man-made objects that may assist in their detection, however, is that they emit and reflect near-infrared radiation that is more highly polarized than does natural background that may include trees, brush grass or terrain.

There are two broad categories of infrared systems designed for military use; namely, scanning system and staring system. However, infrared sensors for extant missile seekers and forward-looking infrared (FLIR) sensors lack the capability for detecting the polarization orientation of the incident radiation, i.e. they respond to any polarization orientation vector of the incident radiation. Studies have shown that the capability to detect and analyze the polarization orientation of near-infrared radiation emanating or reflecting from targets and background scenery can provide a potential means for improving the detection and discrimination of the targets in military systems. Infrared instrumentation having this feature would also have potential commercial applications in areas such as pattern recognition, materials characterization and analysis.

Thus, one way to improve the performance of target detection system is to utilize polarized infrared signatures of a given scenery. What renders this possible is that polarization properties are independent of target-background contrast (i.e. polarization properties are distinct even when there is no temperature difference between the target and the background) and of normal infrared target and clutter temperature fluctuations (i.e. standard deviation of temperature). As is well-known, the formal characterization of an electromagnetic wave that may be linear, elliptical or circular is accomplished with the derivation of the four Stokes parameters.

SUMMARY OF THE INVENTION

This invention relates to a system for detecting and processing passive and active polarized near-infrared radiation for applications in devices such as research, instrumentation, surveillance systems, infrared missile sensors or seekers, search and acquisition systems and guidance systems.

Polarimetric processing capability is added to a typical sensor so that a target object can be more clearly distinguished from the background clutter in a given scenery. An embodiment to accomplish this involves using a polarizer with several segments of different polarization orientations in conjunction with the microchannel image intensifier tube as taught by David B. Johnson, et al in U.S. Pat. No. 5,373,320 (Dec. 13, 1994), resulting in improved sensors. The polarization segments are sequentially advanced to pass therethrough infrared radiation of pre-selected polarization orientations, which radiation, then, impinges on the charge coupled device (CCD) camera. Multiple polarized frame grabbers coupled to the camera produce image frames of the respective pre-selected polarization orientations and image processing circuit then processes these image frames to yield the polarization difference between any given pair of orthogonal polarizations. The polarization differences are subsequently used to enhance the distinction of the objects against the background clutter suspended in the propagation path.

In a surveillance system many such sensors placed to observe diverse geographical locations can be connected to a control center that controls and coordinates the functions of the individual sensors. Also, the control center receives relevant polarization information from the sensors and correlates the information for a more effective surveillance of the diverse locations.

DESCRIPTION OF THE PREFERRED EMBODIMENT

Figure 1:
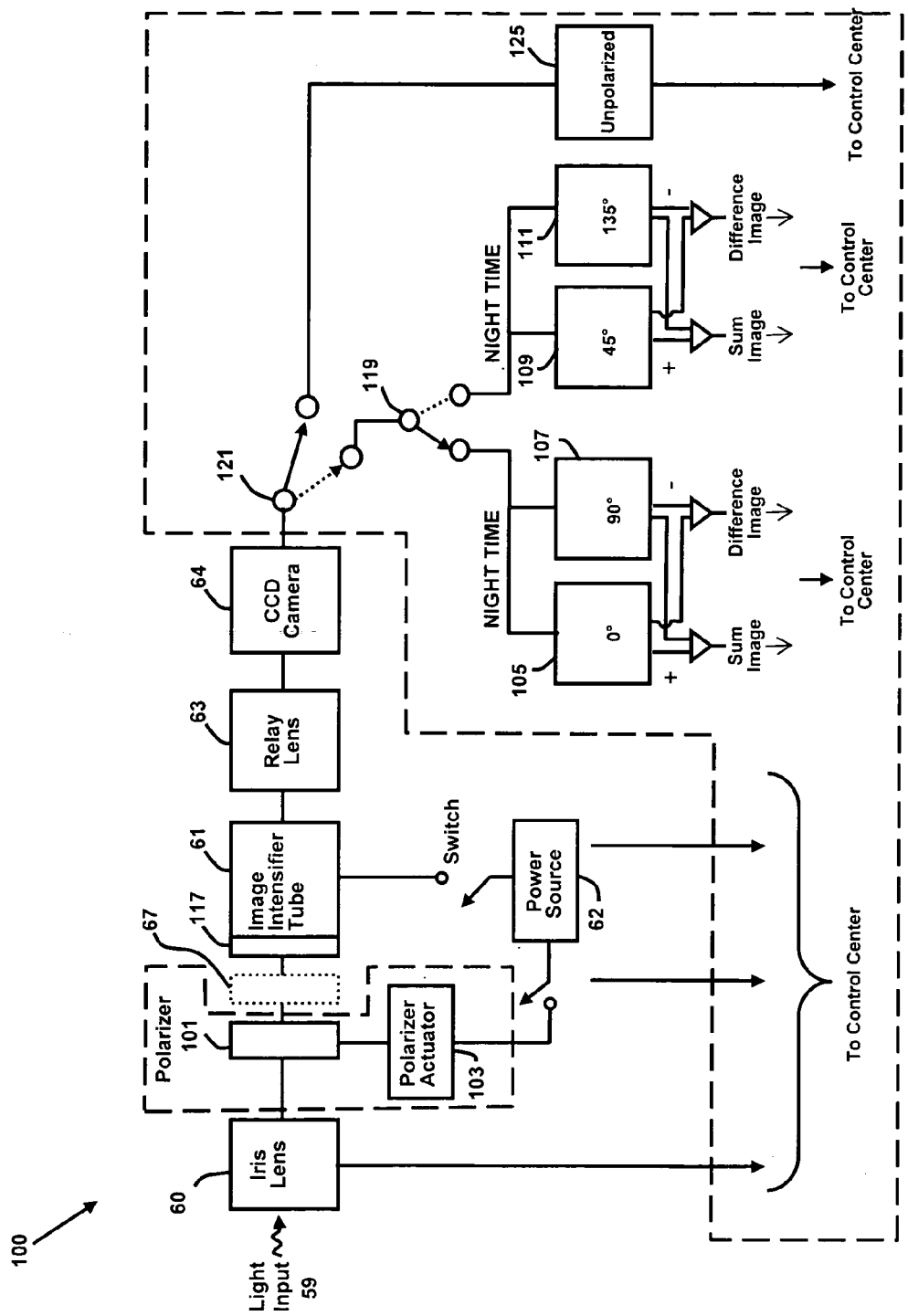
FIG. 1 shows a diagram of a preferred embodiment of the improved sensor, the parts enclosed in the dashed lines indicating the improvement over the Johnson system.

This invention is an improvement that may be used with the camera attachment that converts a standard daylight video camera into a day/night-vision video camera as taught by Johnson in the U.S. Pat. No. 5,373,320 (Dec. 13, 1994). Therefore, the disclosure of the Johnson patent is incorporated herein in its entirety.

Referring now to the drawing wherein like numbers represent like parts in each of the several figures, the improvement to impart differential polarization capability to sensor 100 is explained in detail. Any and all of the numerical dimensions and values that follow should be taken as nominal values rather than absolutes or as a limitation on the scope of the invention.

Figure 2:
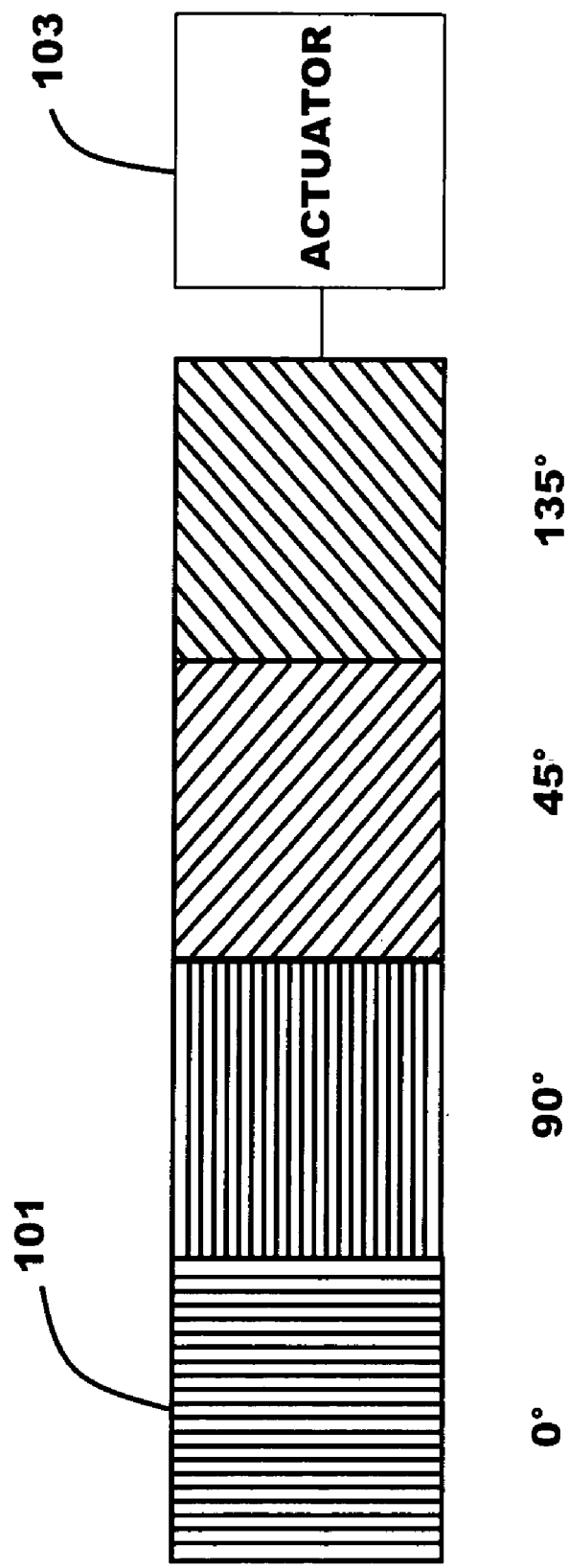
FIG. 2 illustrates the several polarization segments of the polarizer 101.

In FIG. 1, near-infrared radiation 59 emanating or reflecting from the observed scenery (not shown in the figure) enters sensor 100 through iris lens assembly 60 which may be an auto iris lens. At a pre-selected low level of ambient illumination (usually night-time or a very dark day), image intensifier tube 61 having coupled thereto photocathode 117, and polarizer 101 swing into place to be in the path of the incoming radiation 59. The radiation then impinges on polarizer 101, a particular segment of the polarizer having a specific polarization orientation being in the path of the incoming radiation. The particular segment is one of several segments of the polarizer, each segment having a distinct polarization orientation and transmitting only the portion of the incoming radiation that has the same polarization orientation as that of the particular segment in the radiation path. As illustrated in FIG. 2, the several segments of polarizer 101 comprise four at 0°, 45°, 90°, and 135° orientations, respectively. Actuator 103, powered by power source 62, translates the polarizer segments sequentially in discrete steps along the length of image intensifier tube 61 so that they are sequentially engaged to be in the radiation path between iris lens assembly 60 and the image intensifier tube, which may be a two-dimensional microchannel plate.

The radiation transmitted through the engaged polarizer segment is then brought to a focus on photocathode 117 that covers all the pixel elements of the microchannel plate (image intensifier tube). It is noted here that the particular segment of the polarizer engaged at any given moment in time should be sufficiently large to cover all the pixel elements of the microchannel plate. For each pixel element of the radiated image, electrons are emitted from the rear of the photocathode. The electrons thusly emitted from each pixel position enter the corresponding channels of the microchannel plate and are multiplied in the channels of the microchannel plate, subsequently exiting as output light from the microchannel plate and being relayed by the relay lens 63 to be incident on CCD camera 64.

A plurality of polarized frame grabbers 105, 107, 109 and 111, each with a different polarization orientation, are selectively connected to the CCD camera via first switch 119 and second switch 121. The operation of the switches is synchronized with the operation of actuator 103 such that the polarization orientation of the engaged polarizer segment is the same as that of the connected polarizer frame grabber. In exemplar operation of the above-described process, the image at 0° is read into frame grabber 105; then the actuator translates the polarizer to engage the 90°-segment, resulting in the image at 90° being read into frame grabber 107. Then the logic circuitry at the output of the two polarized frame grabbers forms both the sum, $V_0+V_{90}$, and the difference, $V_0+V_{90}$, of the two orthogonal polarizations. From this, the normalized ratio is formed:

$$\text{Polarization Difference} = \frac{V_0 - V_{90}}{V_0 + V_{90}}$$

This information is transmitted to control center 300 for further processing as will be explained below. Collecting two orthogonal polarizations of an object image and differentiating between the two as illustrated above improves the detectability of the object. This process is known as polarization difference imaging and its general principles are explained in U.S. Pat. No. 5,975,702 (Nov. 2, 1999). The process of summation and differencing and obtaining the ratio can be performed with any other pair of orthogonal polarizations.

Since the polarizer functions with the microchannel plate that amplifies the low light level, a condition that is prevalent in night-time, the polarizer is not operational during daylight operation of the sensor, but is removed from the path of the incoming radiation. Thus, at a selected higher level of ambient illumination, under the control of control center 300 the image intensifier tube (microchannel plate) and the polarizer are rotated out of position and, in their place, optical path length compensator 67 is rotated into position and second switch 121 connects the CCD camera with unpolarized frame grabber 125. With the compensator in place, unpolarized imagery may now be collected by the unpolarized frame grabber and further processed by the control center.

Figure 3:
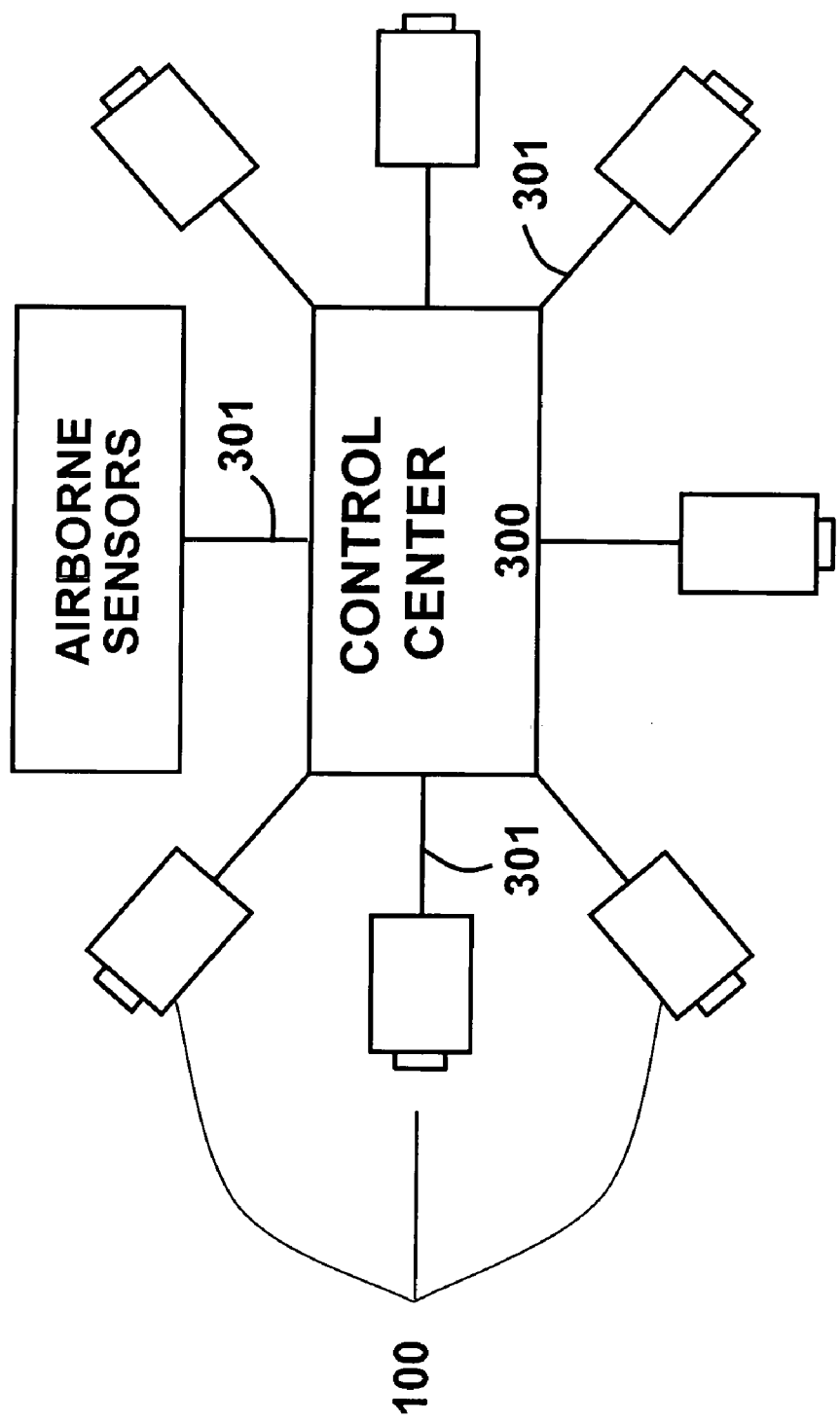
FIG. 3 depicts a surveillance network comprising a plurality of the sensors.

A plurality of ground sensors 100 (perhaps placed along a defensive perimeter to detect hostile intrusion by man or vehicles) may be connected via wireless links or fiber optic links 301 to control center 300 as depicted in FIG. 3 to form a surveillance network. Additional sensors (having the same or different capabilities as the ground sensors) on air-borne platforms may be connected to the control center as well for greater versatility of the network. In such a network, the control center performs correlation of the imagery inputs from the ground sensors with each other as well as with imagery inputs from air-borne sensors and other sources, such as satellites, to identify and track a target object against background clutter. For example, the satellite or air-borne sensors, having the capability to view a large area from their elevated positions, can alert the ground sensors to hostile movements toward the protected perimeter. The ground sensors, on the other hand, having visibility underneath vegetation canopy, may be able to alert the elevated sensors to movements hidden from their view. In addition to transmitting data from the sensors to the control center, links 301 also allows the control center to adjust the settings at each of the sensors: for example, the frame readout rates of each sensor, the selective connections of switches 119 and 121, the occasional activation of power source 62 and the level of incoming radiation through iris lens assembly 60.

Figure 4:
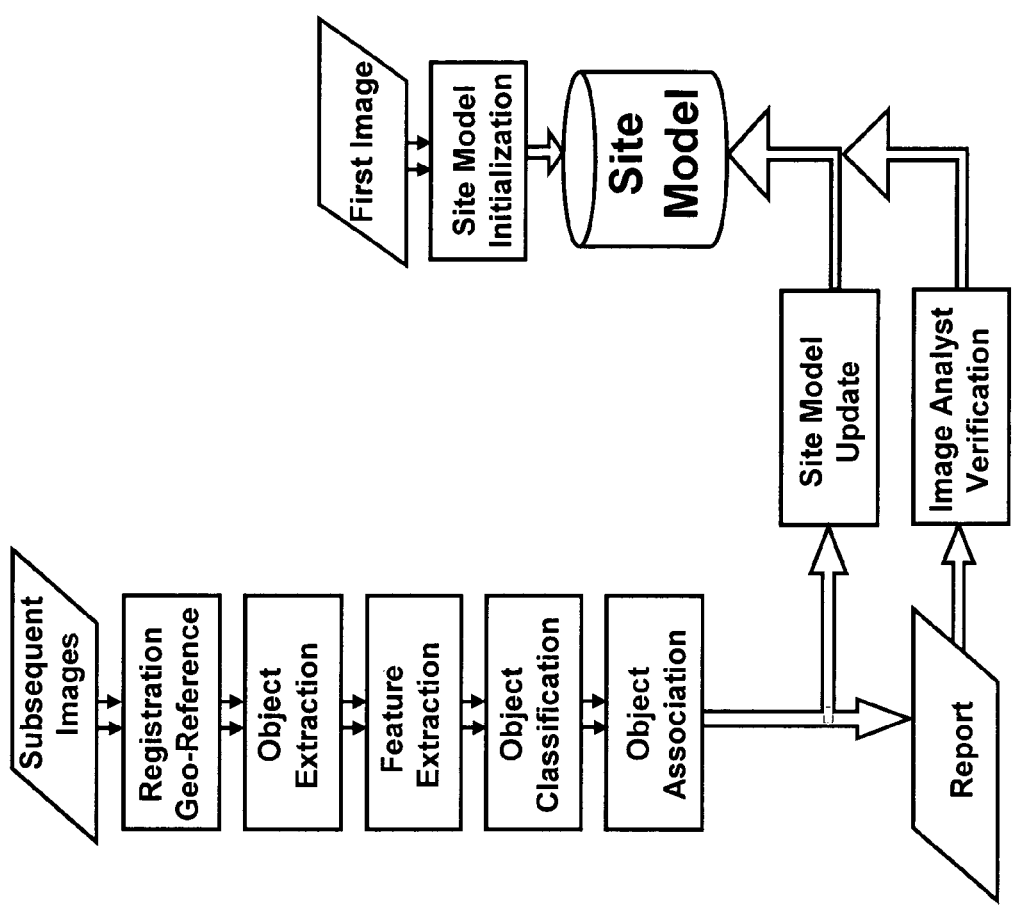
FIG. 4 is a flowchart of a typical algorithm that may be used by control center 300 to process the inputs from individual sensors 100.

It is assumed that the control center is under the supervision of an expert image analyst, as indicated in FIG. 4, who is familiar with the topography and understands the physics of the diurnal and long term changes in the scenes observed, even though the image processing operations may be performed autonomously or semi-autonomously. The terrain features being observed by the sensors in the surveillance system may include natural and man-made features both of which change over time. The scenes being observed may include roads (a target area for emplacement of roadside bombs), building structures that may conceal snipers, a forest area that might conceal military movement or grassy area where land mines may be buried. In all these applications, the scene images are obtained at different points in time that may extend over a period of an hour to a day, or a period of a day to weeks or to months. This requires that a signal model of each of the emplaced sensors be developed so that variations can be identified, and imperfections in time be obtained to compensate for those variations in each sensor. A suitable calibration procedure is described by Mehrdad Soumekh et al in "Time Series Processing of FLIR Imagery for MTI and Change Detection" in the IEEE's *Proceedings of the International Conference on Acoustics, Speech and Signal Processing*, Vol. 5, pages 21–24 (2003). The calibration procedure is performed under the supervision of the control center and its result becomes a part of the site model as depicted in FIG. 4.

Initially, to build the site model, an aerial image of a site (a given scene) is obtained as a reference. Then subsequent images of the site from emplaced ground sensors or airborne sensors are used to update and verify the site model, utilizing the principle that when two or more images of a given scene are available and the geometric relationship between the images and the geo-spatial coordinates are known with some degree of accuracy, the collected images can be coordinated. FIG. 4 illustrates a representative software architecture for implementing signal processing operation between the multiple images obtained from the several ground emplaced sensors or aerial sensors. It is noted that the aerial sensors and the ground sensors may not be of the same type; it is envisioned that the aerial sensors would include all-weather sensors, such as synthetic aperture radar (SAR), but the ground sensors would not. The aerial sensors may also be hyperspectral sensors whose several spectral bands can be directly coordinated with the ground sensors.

The main operation of control center 300 is achieving the match between images from the same or different sensor types taken at different times and different resolutions. A common approach is to designate one image, an aerial image for example, as a reference and perform a rotation or warping of the second image to bring it into alignment with the reference image. Many algorithms are already known in the art that can be used to coordinate multiple images, depending on the nature of the particular images. For example, when comparing infrared images at wavelengths shorter than 4–5 microns and those at longer infrared wavelengths, a suitable algorithm used to achieve a match between the day-time images and night-time images is the Multivariate Mutual Information Algorithm as is explained in "Registration of Image Cubes Using Multivariate Mutual Information," by Jeffrey P. Kern et al in IEEE's *Thirty-Seventh ASILOMAR Conference: Signals, Systems and Computers,* Vol. 2, pages 1645–1649 (2003). Another example is when the air-borne sensor includes a SAR. In such a case, the fusion of the SAR image with near-infrared image will be the required signal processing. Yet a third example is when the targets are far from the sensors and thus appear in the image as points against the background clutter. In this case, the necessary signal processing may include a multi-scale decomposition based on wavelets that allows the detection and characterization of the dynamic elements in the scene. An algorithm to accomplish such decomposition is explained in "Multiple Single Pixel Dim Target Detection in Infrared Image Sequence," by Mukesh A. Zaveri et al in IEEE's *Proceedings of International Conference on Circuits and Systems,* Vol. 2, pages II-380 to II-383 (2000).

Although a particular embodiment and form of this invention has been illustrated, it is apparent that various modifications and embodiments of the invention may be made by those skilled in the art without departing from the scope and spirit of the foregoing disclosure. For example, to obtain two frames of orthogonal polarizations at the same instant in a given sensor, one can use a stereo camera with the two orthogonal polarizers fixed to the two separate sets of optics so the two frames of orthogonal polarizations are obtained at the same instant. This may avoid the image smearing that can happen if motion occurs during the transition of the polarizer from one polarization segment to another but would correspondingly require additional intensifier, relay lens and switching mechanism, rendering the system bulkier and more complicated. Another modification is to use sensors that are capable of switching between daylight and night vision operational modes. To provide differential polarization during daylight operations, a second polarizer-actuator assembly would need to be integrated with the optical elements of the sensor. Accordingly, the scope of the invention should be limited only by the claims appended hereto.

I claim:

1. In a system for viewing a pre-selected scenery in the near-infrared spectrum, the system having an iris lens assembly for collecting incoming radiation, a charge-coupled device camera; a relay lens for focusing the collected radiation onto the CCD camera; a microchannel image intensifier positioned between the iris lens assembly and the relay lens, an optical path length compensator selectively-placeable between the iris lens and the image intensifier, the intensifier amplifying the incoming radiation level prior to transmitting the radiation to the relay lens; and a photocathode coupled to the image intensifier, AN IMPROVEMENT for providing a polarimetric processing capability to the system so as to enable distinction of various features of the pre-selected scenery, said IMPROVEMENT comprising: a polarizer placeable between the iris lens and the photocathode, said polarizer being composed of several discrete segments of different polarization orientations and being translatable along the length of the image intensifier in discrete steps so as to bring sequentially said discrete polarization segments to be engaged between the iris lens and the photocathode, each of said segments being of sufficient size to cover all the pixels of the image intensifier; a plurality of polarized frame grabbers coupled to the CCD camera, each polarized frame grabber receiving radiation of a particular polarization orientation and outputting an image frame of that particular polarization orientation; and a logic circuit for performing image processing on said image frame outputs from said polarized frame grabbers and producing therefrom polarization difference of any given pair of orthogonal polarization orientations, said polarization of difference being used to enhance the visual perception of the diverse features of the scenery.

2. An IMPROVEMENT as set forth in claim 1, wherein said improvement further comprises: a means to translate said polarizer in said sequential manner along the length of the image intensifier.

3. An IMPROVEMENT as set forth in claim 2, wherein each of said several discrete segments of said polarizer covers all of the pixel elements in the microchannel image intensifier.

4. An IMPROVEMENT as set forth in claim 3, wherein said improvement still further comprises: a first switch coupled between the CCD camera and said polarized frame grabbers, said first switch selectively connecting, from time to time, said CCD camera with one of said polarized frame grabbers.

5. An IMPROVEMENT as set forth in claim 4, wherein said first switch is selectively connected to said polarized frame grabbers in synchronization with said translating means such that, at any given moment in time, said engaged polarization segment and said connected polarized frame grabber are of the same polarization orientation.

* * * * *